Figure 5:
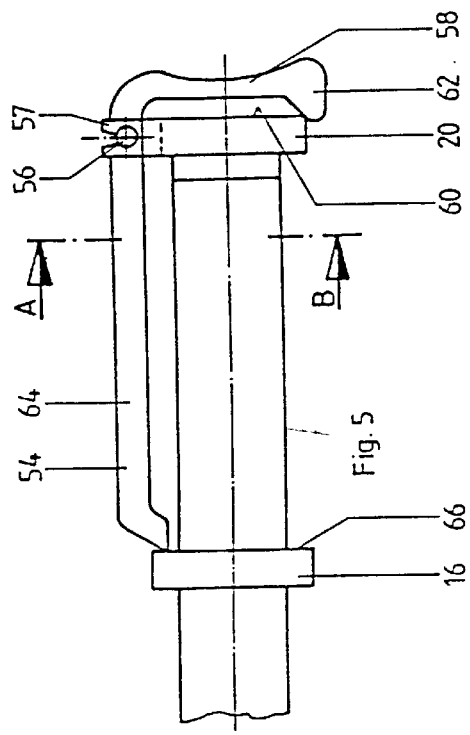

United States Patent

Schlegel et al.

[11] Patent Number: 5,810,769
[45] Date of Patent: Sep. 22, 1998

[54] CANNULA FOR THE SUBCUTANEOUS DEPOSITION OF AN OBJECT

[75] Inventors: Karl-Heinz Schlegel, Langenselbold; Herbert Feit, Wächtersbach, both of Germany

[73] Assignee: Süddeutsche Feinmechanik GmbH, Germany

[21] Appl. No.: 696,976

[22] PCT Filed: Feb. 27, 1995

[86] PCT No.: PCT/EP95/00713

§ 371 Date: Aug. 23, 1996

§ 102(e) Date: Aug. 23, 1996

[87] PCT Pub. No.: WO95/23010

PCT Pub. Date: Aug. 31, 1995

[30] Foreign Application Priority Data

Feb. 25, 1994 [DE] Germany .................. 94 03 161 U

[51] Int. Cl.⁶ .................................................. A61M 31/00
[52] U.S. Cl. ................................ 604/59; 604/57; 604/60; 604/264; 606/117
[58] Field of Search .................... 604/59, 57, 11, 604/15, 18, 60, 62, 891.1, 264, 272, 200, 209, 210, 158; 606/117

[56] References Cited

U.S. PATENT DOCUMENTS 5,725,504  3/1998  Collins .................................. 604/165

*Primary Examiner*—Mark Bockelman
*Assistant Examiner*—N. Kent Gring
*Attorney, Agent, or Firm*—Bierman, Muserlian and Lucas

[57] ABSTRACT

A cannula for deposition of an object in the body of a living organism, comprising a cannula holder having a first handle and a sleeve with a second handle surrounding said cannula holder at least in part and being axially movable in relation thereto, and having a mandrin extending inside the cannula, said object such as a medical long-term preparation, identification carrier or capsule containing a radioactive substance being depositable by a relative movement between the mandrin and the cannula receiving the object.

19 Claims, 3 Drawing Sheets

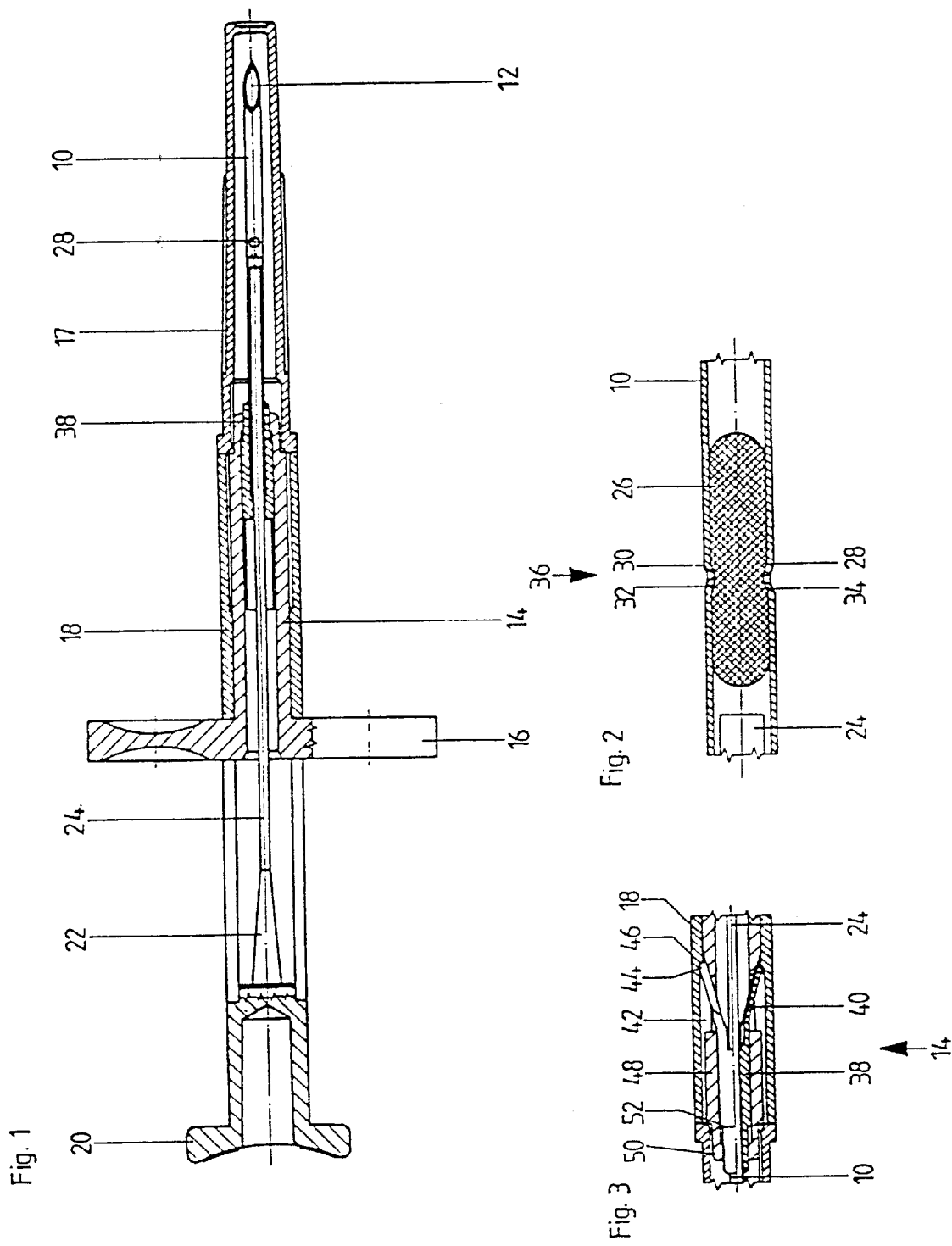

Schnitt A-B

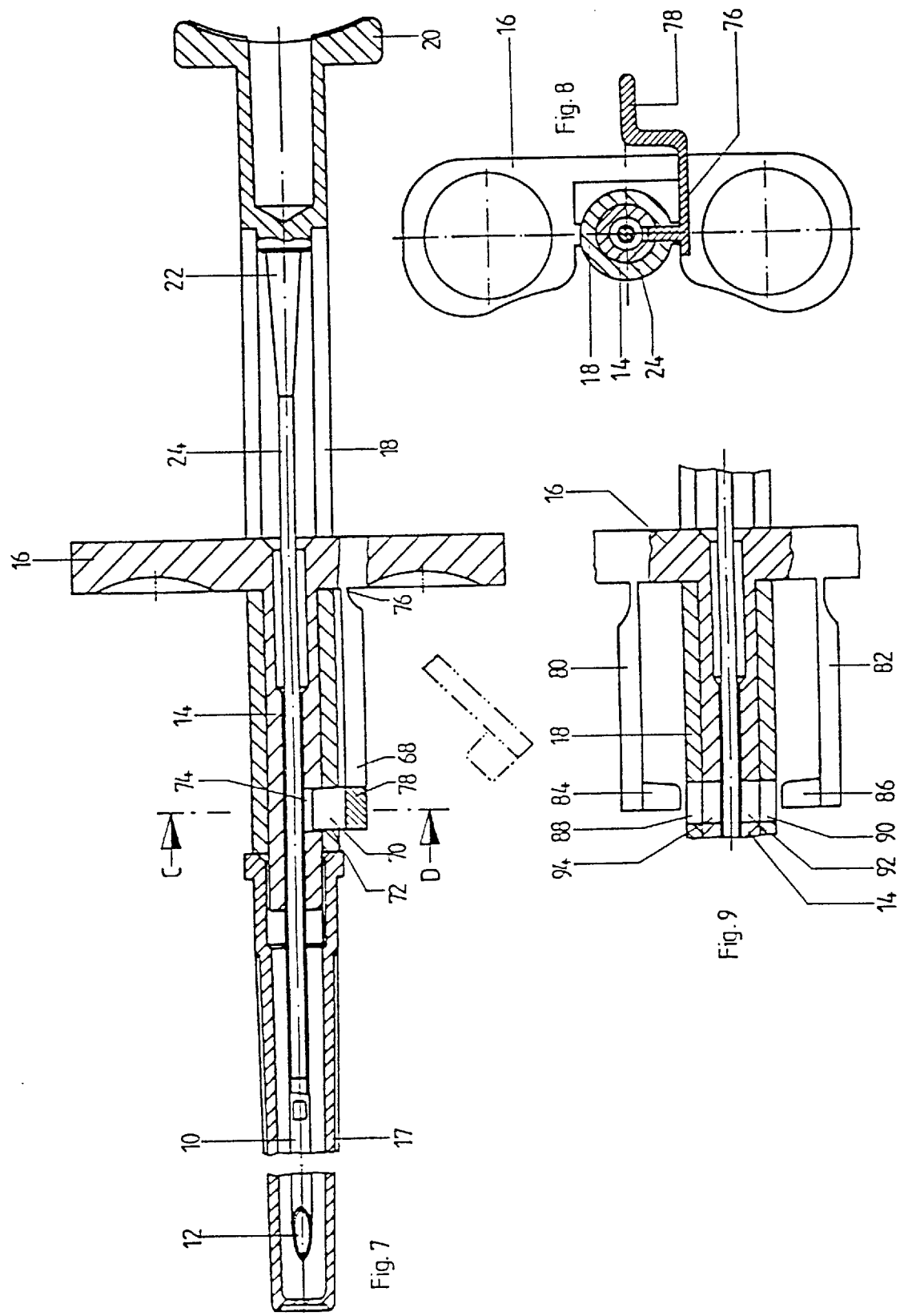

CANNULA FOR THE SUBCUTANEOUS DEPOSITION OF AN OBJECT

The invention relates to a cannula for deposition of an object in the body of a living organism, comprising a cannula holder having a first handle and a sleeve with a second handle surrounding said cannula holder at least in part and being axially movable in relation thereto, and having a mandrin extending inside the cannula, said object such as medical long-term preparation, identification carrier or capsule containing a radioactive substance being depositable by a relative movement between the mandrin and the cannula receiving the object.

A cannula of this type is shown in WO 92/15362. It was possible for the first time with an appropriate cannula to arrange the object before deposition in a previously known position in order to simplify implantation and to ensure deposition in a required tissue. The position was fixed in particular by a closure closing the cannula at the cannula tip end at least partially and having the form of a salve-like material containing a medical agent, or an adhesive material or silicone plug.

Due to the type of position fixing, foreign matter is introduced into the body during implantation of the object, which might lead to undesirable or unexpected reactions.

Further cannulas for deposition of solid or semi-solid preparations under the skin of a living organism are known for example from U.S. Pat. Nos. 4,900,304, 4,950,234 or EP 0 255 123 A2.

EP 0 304 107 A1 describes an injection cannula for deposition of an implantate, where the cannula itself is intended for once-only use.

According to U.S. Pat. No. 4,820,267, an implantate is position-fixed solely for transport purposes inside a cannula using a mandrin and—distally—using a pin. To prevent the pin from slipping out of the cannula uncontrolled, the pin is fixed on the outside by a protective envelope.

A flexible cannula for the identification of animals is provided in accordance with WO 90/05488, the distal area of which has a smaller cross-section than that in which a mandrin is slidable.

A cannula of the type described at the outset is known from U.S. Pat. Nos. 4,846,793 or 4,994,028, in which the sleeve is designed rotatable relative to the cannula holder in order to achieve mutual engagement. This has the drawback that the insertion of the cannula and subsequent deposition of the object can as a rule only be achieved with two hands.

The object of the present invention is to develop a cannula of the type mentioned at the outset such that on the one hand a problem-free and flawless fixing of the position of the object to be implanted is possible without the need for foreign substances that might penetrate into the body inside which the object is to be implanted. There should also be the possibility of checking the position of the object in simple fashion, even if the cannula consists of non-transparent material, in particular metal. On the other hand, it should be possible to perform insertion of the cannula into the body and subsequent deposition of the element by withdrawing the cannula using one hand.

As regards the possibility for one-hand operation, the object is achieved in that when pressure is applied to the second handle extending from the sleeve, the latter with the cannula holder can be engaged by at least one spreader element extending from this cannula holder or by an engaging or lever element extending from the cannula holder or sleeve.

This measure ensures that during insertion of the cannula into the body it then cannot move—or if so only slightly—relative to the sleeve and hence to the mandrin when the pressure necessary for insertion comes from the sleeve, i.e. the second handle such as the grip.

To deposit the object, it is then only necessary for axial movement of the cannula holder in the direction of the second handle, as a result of which either the engaging element extending from the cannula holder disengages automatically from the sleeve or the lever element is disengaged in controlled form from the sleeve by the hand pulling the cannula holder axially in the direction of the second handle.

In particular, it is provided that the cannula holder comprises an immovable shoulder surrounding the cannula and a sleeve body surrounding said shoulder and axially movable relative thereto and incorporating the first handle, that at least one spreader element extends from the shoulder, passes through the sleeve body and rests against a section of the sleeve when pressure is applied to the second handle, and that during movement of the first handle in the direction of the second handle the sleeve body disengages the spreader element from the section and moves the shoulder too.

Alternatively, it is possible that a swivelable engaging element such as a lever extends from the sleeve and can be rested against the cannula holder or its handle.

Here the engaging element is preferably an angled lever whose short leg is in the area of the second handle, preferably along its outer surface facing away from the cannula, and whose longer leg can be rested with its free end on that side of the first handle facing away from the cannula.

The angled lever can here be clampable in a receptacle extending from the second handle and forming the swivel axis for the angled lever.

To permit easy swiveling of the angled lever, the short leg should rest on the second handles with its free end part and run between the receptacle and the support at a distance from the second handle. To disengage the long leg from the cannula holder or its grip, all that is necessary then is for pressure to be exerted on the short leg, which automatically moves the long leg away from the cannula. The short leg can be firmly engaged with a section, preferably with its free end on the second handle, thereby ensuring that uncontrolled swiveling back of the angled lever is not possible.

A further independent proposal for solution provides that a lever element passing along the outside of the sleeve and engageable therewith extends from the cannula holder. In this case, the lever element can be connected to the first handle preferably by a hinge such as a film hinge. For swiveling—i.e. disengagement from the sleeve—a handle such as a projection extends from the lever element and is gripped whenever the element is no longer to engage with the sleeve. The lever element preferably extends tangentially in the sleeve—but a radial direction is also possible—with the handle running in this area of the lever element and projecting beyond the sleeve.

The lever element itself can be locked in the sleeve by its end projection, where the end projection passes through the sleeve when the cannula holder is locked to the sleeve and engages in a recess of the cannula holder.

Although the lever element is preferably spring-pretensioned in the direction of the sleeve preferably by virtue of the material, thereby resulting in automatic engagement between the cannula holder and the sleeve when the cannula is inserted, an alternative possibility is that the lever element is at a distance from the sleeve when no force is exerted, with the result that engagement must be in controlled manner.

Regardless of the design of the engagement mechanism, however, there is always the possibility of using one and the same hand for insertion of the cannula by pressure exertion on the second handle, for disengagement/unlocking and for withdrawal of the cannula by pulling back the grip in the axial direction of the cannula. Disengagement/unlocking can take place automatically either by using spreader elements or by suitable fixing of the lever element in the sleeve or cannula holder whenever the lever element remains engaged during pressure exertion on the second handle, but is released from its locked state when the first handle is pulled in the direction of the second handle. Naturally end locking can also be achieved by controlled movement or adjustment of the lever element.

To solve the partial aspect of the invention relating to problem-free and flawless position fixing of the object to be implanted, it is proposed that the object having yielding properties at least on the outside be clamped by a section of the cannula in which the cannula has a cross-section or aperture differing from that provided between the object and the cannula tip. Here the cross-section reduction can be achieved by a bead surrounding it at least in parts. However, other methods are also possible for a change in the cross-section by dimpling of a cannula wall section or by formation of an aperture. Compression of the cannula is also feasible to achieve the cross-section change by which the object to be implanted is clamped.

In addition, an aperture as vision panel can be provided in the area of that section of the cannula clamping the element, by which the cross-section change itself or an area is fixed in which the object can expand, thereby also fixing the position.

With the teachings in accordance with the invention, it was possible in simple manner to fix the position of the object by altering the cross-section of the cannula in that area in which the object is to be fixed in position before it is implanted. Since the object to be implanted has at least on the outside yielding or elastic properties, secure clamping is possible without the risk of damage to the object, particularly when medical or radioactive preparations are enclosed by the outer envelope.

Further details, advantages and features of the invention are shown not only in the claims and in the features therein, singly and/or in combination, but also in the following description of preferred embodiments shown in the drawing.

Figure 6:
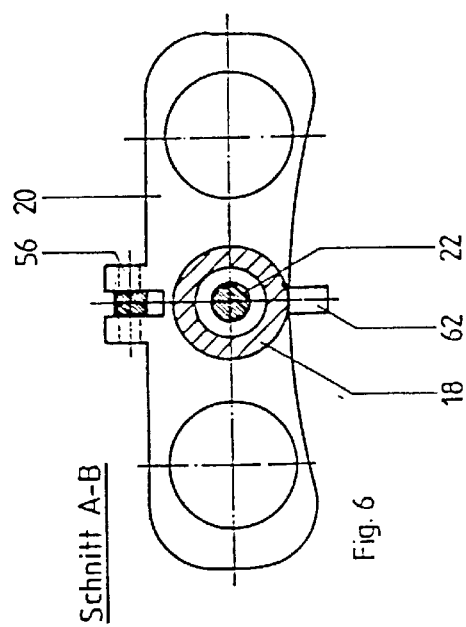
Figure 4:
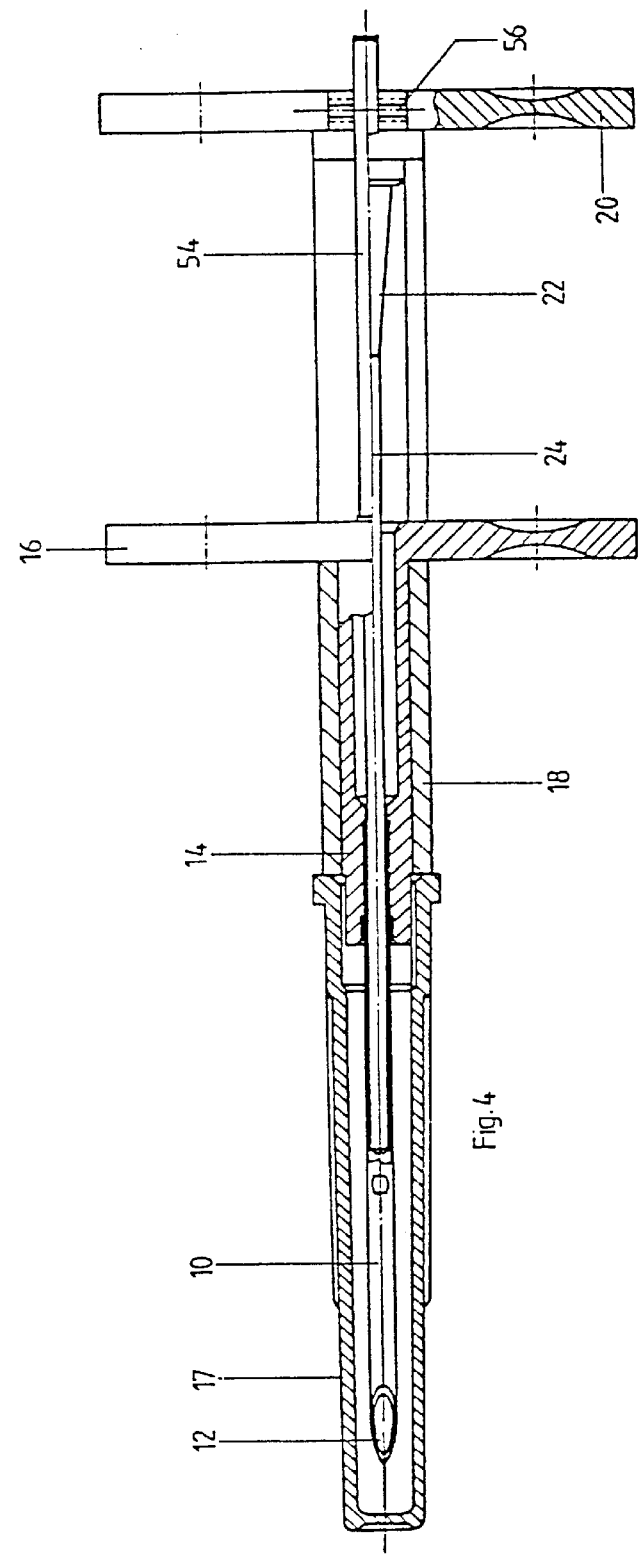

In the drawing,

FIG. 1 shows a section through a cannula for implantation of an object such as a medical preparation or identification carrier, FIG. 2 shows a section of the cannula according to FIG. 1, but in an enlarged view, FIG. 3 shows a further section of the cannula according to FIG. 1, FIG. 4 shows a longitudinal section through a further embodiment of a cannula, FIG. 5 shows a section of the cannula according to FIG. 4, but rotated 90°, FIG. 6 shows a section along the line A-B in FIG. 5, FIG. 7 shows a third embodiment of a cannula, FIG. 8 shows a section along the line in the direction of line C-D in FIG. 7, and FIG. 9 shows an alternative solution for a locking mechanism for the proposal shown in FIG. 7.

In order to implant in an animal or human body an element such as a medical preparation, in particular a long-term preparation such as Reptid, an encapsulated radioactive preparation (Slak) or an identification carrier, a cannula (10) is used. The cannula (10) can be made of steel, plastic or of any other suitable material with preferably slantingly cut tip (12). The, cannula (10) is mounted in a cannula holder (14) which, in the embodiment, merges into a handle such as grips (16). A sleeve (18) extends in front of and behind such grips (16) and is slotted away from the cannula in order to move an ejection plunger (22) sliding in the longitudinal direction of the cannula (10) and likewise provided with a handle (20) on the outside, said plunger in turn being connected to a mandrin (24) moving in relation to the cannula (10), using which the object (26) not shown in FIG. 1 and shown enlarged in FIG. 2 can be deposited inside a body by relative movement between the mandrin and the cannula. Although the object (26) is preferably deposited by withdrawing the cannula (10), it is of course also possible to deposit it by moving the mandrin (24) in the direction of the cannula tip (12).

The cannula (10) is furthermore surrounded by a protective cap (17) clipped onto the cannula holder (14).

Between the grip (16) and the cannula tip (12), the cannula (10) has a geometric change such as a lumen constriction (28) that can be achieved in a number of ways. For example, the cannula wall can be dimpled or provided with a bead running at least part of the way around. In particular, it is provided—for example by dimpling—that two apertures (28) and (30) are made diametrically opposite to one another and whose inner edges (32) and (34) respectively extend into the interior of the cannula (10), i.e. effecting the required geometry changes or cross-section reductions.

The object (26) to be implanted is now clamped in that section (36) of the cannula (10) having the cross-section changes. To this end, it is necessary for the object to have yielding or elastic properties at least on the outside to ensure that the object itself is not damaged, e.g. that preparations of radioactive substances contained in an envelope cannot leak out in uncontrolled form.

As is to be made clear in FIGS. 1 and 2, the apertures (28) and (30) also provide the possibility of visually checking the clamped object (26), i.e. they have the function of vision panels. The object can also press into the apertures (28) and (30) and thereby fix the position. Additional lumen changes are not necessary in this case.

To permit both insertion of the cannula and deposition of the object (26) with only one hand, it is possible in accordance with the invention for the sleeve (18) to be engaged relative to the cannula (10) and hence to the cannula holder (14) during insertion, whereas during subsequent withdrawal of the cannula (10), i.e. movement of the grip (16) in the direction of the handle (20), only an axial movement is necessary.

To permit this engagement, various solutions are possible.

For example, the cannula shoulder (38) can have spreader elements (40) whose free ends (44) extend in the direction of the grip (16) and project flexibly outwards in the direction of the sleeve, with the free end (44) of the spreader element (40) being in contact with a section such as an ledge (46) of the inner wall of the sleeve (18) when pressure is exerted on the handle (20).

To that end, the spreader elements (40) extend from a cannula shoulder (38) immovably surrounding the cannula (10) and surrounded by a sleeve body (48) incorporating the grip (16).

The cannula shoulder (38) and the sleeve body (48) form the cannula holder (14), with the spreader element (40) being able to pass through an aperture (42) in the sleeve body (48) when the free end (44) of the spreader element (40) is to be in contact with the ledge (46) of the sleeve (18).

If the object (26) is to be deposited, the grip (16) is pulled back axially as already mentioned, as a result of which the sleeve body (48) first moves along the cannula shoulder (38) before an annular projection (50) of the sleeve body (48) comes up against a step (52) of the cannula shoulder (38) and moves this shoulder along too during further axial movement of the cannula holder (14).

The initial relative movement between the sleeve body (48) and the cannula shoulder (38) in the direction of the free end (44) of the spreader element (40) bends the latter towards the cannula (10) such that the free end (44) disengages from the ledge (46) of the sleeve (18). As a result, the cannula holder (14) can be moved axially relative to the sleeve (18).

Other possibilities for locking between the sleeve (18) and the cannula holder (14) are shown in FIGS. 4 to 9. This has the advantage that the cannula holder (14) with its section slidable inside the sleeve (18) no longer has to be designed in several parts, i.e. does not contain sections movable relative to one another as is the case in the embodiment in FIGS. 1 and 2.

In the embodiment in FIGS. 4 to 6, an angled lever (54) extends from the grip (20) of the sleeve (18) containing the ejection plunger (22), and can be rested on the grip (16) of the cannula holder (14) such that when pressure is exerted on the grip (20) in the direction of the cannula tip (12), the sleeve (18) and the cannula holder (14) are axially movable as a single unit.

The angled lever (54) swivels about an axis (56) formed by a receptacle (57) in which the angled lever (54) engages. The receptacle (57) extends from the grip (20) of the sleeve (18).

The short leg (58) of the angled lever (54) extends along that surface (60) of the grip (20) facing away from the cannula tip (12) and is at a distance to this grip in some areas. The short leg (58) has a preferably bulbous end section (62) which can then engage in the grip (20) if the angled lever (54) is to be unlocked in the manner described in the following. Alternatively, it is possible to lock the angled lever (54) using—for example—its short leg (58) such that an uncontrolled swivel movement of the angled lever (54) is ruled out.

It is of course not essential that the short leg (58) is locked at any time. The leg should however initially rest on the grip (20).

Provided no pressure is exerted on the short leg (58) of the angled lever (54), the latter with its long leg (64) is in contact with the outside (66) of the grip (16), as shown in FIG. 5, or is locked with this. As a result, insertion of the cannula (10) into tissue can take place without the cannula (10) moving relative to the grip (20) and hence to the mandrin (24). If the object (26) located inside the cannula (10) is to be deposited, a pressure is exerted on the short leg (58) of the angled lever (54) or the latter is unlocked, so that as a result the long leg (64) is swiveled outwards about the axis (56) and hence disengages from the grip (16). The object (26) can then be deposited by axial withdrawal of the grip (16), since the mandrin (24) holding the object (26) remains in place while the cannula (10) is withdrawn in relation thereto.

Locking as per the embodiment in FIGS. 7 to 9 is by means of a lever (68) extending from the grip (16) of the cannula holder (14) and able to engage tangentially or radially in a matched recess (72) of the sleeve (18) with an end section (70) in the form of a projection extending in the direction of the cannula (10). In this case the section (70) can preferably pass completely through the sleeve (18) and engage in a recess (74) of the cannula holder (14) in order to strengthen the locking action, particularly when the wall of the sleeve (18) is thin.

The lever element (68) is preferably connected via a type of film hinge (76) to the grip (16) and spring-pretensioned in the direction of the sleeve by virtue of the material. In this case, the projection (70) attempts at all times to be in contact with the sleeve (18).

To permit unlocking, i.e. removal of the lever (68) from the recesses (72) and (74), a handle extends from the lever (68) or projection and runs along the side of the sleeve (18) and/or projects radially so that gripping of the handle such as the projection (78) does not disengage the lever element (68) from the sleeve (18).

Alternatively to the embodiment in FIG. 7, lever elements (80), (82) running diametrically opposite to one another can extend from the grip (16), which are however not pre-tensioned in the direction of the sleeve (18); instead they are with their end sections (84), (86) extending in the direction of the sleeve (18) at a distance from the outer surface of the latter. If locking is required, pressure must be exerted on the levers (80), (82) in the direction of the sleeve (18) so that the projections (84), (86) engage in corresponding recesses (88), (90) or (92), (94) of the sleeve (18) or cannula holder (14) respectively.

We claim:

1. A cannula (10) for deposition of an object (26) in the body of a living organism, comprising a cannula holder (14) having a first handle (16) and a sleeve (18) with a second handle (20) surrounding said cannula holder (14) at least in part and being axially movable in relation thereto, and having a mandrin (24) extending inside said cannula and a fixation means, said object being depositable in the body by a relative movement between said mandrin and said cannula (10) receiving said object, characterized in that when pressure is applied to said second handle (20) extending from said sleeve (18) the latter can be engaged with said cannula holder (14) by said fixation means of at least one spreader element (40) extending from said cannula holder or by an engaging or lever element (54, 68, 80, 82) extending from said cannula holder or said sleeve.

2. A cannula according to claim 1, characterized in that said cannula holder (14) comprises an immovable cannula shoulder (38) surrounding said cannula (10) and a sleeve body (48) surrounding said shoulder and axially movable relative thereto and incorporating said first handle (16), in that at least one spreader element (40) extending away from the cannula tip (12) and in the direction of said sleeve (18) extends from said cannula shoulder and rests against a section (46) of said sleeve when pressure is applied to said second handle, and that during movement of said first handle extending from said cannula holder (14) in the direction of said second handle said sleeve body disengages said spreader element from said section and moves said shoulder too.

3. A cannula according to claim 1, characterized in that a swiveling engaging element such as a lever (54) extends from said sleeve (18) and can rest against said cannula holder (14) or its handle (16).

4. A cannula according to claim 3, characterized in that said engaging element is an angled lever (54) with a short leg (58) in the area of said second handle, preferably along its outer surface (60) facing away from said cannula (10).

5. A cannula according to claim 4, characterized in that said short leg (58) of said angled lever (54) should rest on and/or engage with said second handle (20) at its free end part (62) and run between said rest/engaged connection and said swivel axis (56) at a distance from said outer surface (60) of said second handle (20).

6. A cannula according to claim 1, characterized in that said lever (54) is angled and can here be clampable in a receptacle (57) extending from said second handle (20) and forming the swivel axis (56) for said angled lever.

7. A cannula according to claim 1 at least characterized in that a lever element (68,80,82) extending from the cannula holder (14) running on the outside along said sleeve (18) and engageable therewith.

8. A cannula according to claim 7 at least, characterized in that said lever element (68) is connected to said first handle (16) preferably by a hinge such as a film hinge (76) and can be gripped and swiveled by a handle (78) running radially or laterally to said sleeve (18).

9. A cannula according to claim 1, characterized in that said lever element (68) is lockable in said sleeve (18) by a projection (70) at its end.

10. A cannula according to at least one of the preceding claims, characterized in that when said cannula holder (14) is locked relative to said sleeve (18) said end projection (70) of said lever element (68) passes through said sleeve (18) and engages in a recess (74) of said cannula holder.

11. A cannula according to at least one of the preceding claims, characterized in that said lever element (68) is spring-pretensioned in the direction of said sleeve (18) preferably by virtue of the plastic or metal material.

12. A cannula according to at least one of the preceding claims, characterized in that said lever element (80, 82) is at a distance from said sleeve (18) when no force is exerted on the latter.

13. A cannula according to claim 1, characterized in that two lever elements (80, 82) extend from said first handle (16).

14. A cannula according to preferably claim 1, characterized in that said object (26) having yielding properties at least on the outside is clamped by a section (36) of said cannula (10) in which said cannula has a cross-section or aperture (28, 30) differing from that between said object and said cannula tip (12).

15. A cannula according to claim 14, characterized in that the cross-section or aperture is achieved by a bead surrounding said cannula at least in parts.

16. A cannula according to claim 14, characterized in that the cross-section or aperture is achieved by at least one dimple (28, 30) of a cannula wall section.

17. A cannula according to claim 15, characterized in that said cross-section or aperture is achieved by at least one aperture (28, 30) in a cannula wall section, with an inner edge (32, 34) of said aperture preferably extending into the interior of said cannula.

18. A cannula according to claim 14, characterized in that in the area of said cannula section (36) clamping said object (26) an aperture is provided as a vision panel.

19. A cannula according to claim 14, characterized in that said vision panel is at least one aperture (28, 30) causing the lumen change.

* * * * *